(12) United States Patent
Matsuoka et al.

(10) Patent No.: US 9,689,847 B2
(45) Date of Patent: Jun. 27, 2017

(54) GAS CHROMATOGRAPHY EQUIPMENT

(75) Inventors: Satoshi Matsuoka, Kyoto (JP);
Takahiro Nishimoto, Kyoto (JP);
Masaki Kanai, Kyoto (JP); Masanori Nishino, Kyoto (JP); Masato Morii, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 185 days.

(21) Appl. No.: 14/419,513

(22) PCT Filed: Aug. 7, 2012

(86) PCT No.: PCT/JP2012/070058
§ 371 (c)(1),
(2), (4) Date: Feb. 4, 2015

(87) PCT Pub. No.: WO2014/024253
PCT Pub. Date: Feb. 13, 2014

(65) Prior Publication Data
US 2015/0285769 A1 Oct. 8, 2015

(51) Int. Cl.
*G01N 30/54* (2006.01)
*G01N 30/60* (2006.01)
(Continued)

(52) U.S. Cl.
CPC ............ *G01N 30/54* (2013.01); *G01N 30/30* (2013.01); *G01N 30/6047* (2013.01);
(Continued)

(58) Field of Classification Search
CPC .......... B01D 53/025; G01N 2030/025; G01N 2030/3084; G01N 30/30; G01N 30/54;
(Continued)

(56) References Cited

U.S. PATENT DOCUMENTS 4,057,998 A 11/1977 Moreaux
6,530,260 B1 3/2003 Mustacich et al.

FOREIGN PATENT DOCUMENTS

JP 59-020682 Y2 6/1984
JP 61-028057 U 2/1986
(Continued)

OTHER PUBLICATIONS

International Search Report dated Oct. 30, 2012, issued in corresponding application No. PCT/JP2012/070058.

*Primary Examiner* — Daniel S Larkin
(74) *Attorney, Agent, or Firm* — Westerman, Hattori, Daniels & Adrian, LLP

(57) ABSTRACT

A gas chromatography equipment includes a sample introducer, a detector, a column module, and an oven including a housing. A sub-space is provided in a projection section projecting downward from a portion of a bottom face of the housing communicates with a main space of the housing. A column module attaching section is provided outside the housing and below the main space. A fixed side face, which faces the column module attaching section, of the projection section serves as an attachment face for attaching the column module. The column module is attached to the housing in such a way that the main flat surface of the column module is horizontally positioned with an end face of the column module being the attachment face.

8 Claims, 5 Drawing Sheets

(51) Int. Cl.
 _B01D 53/02_ (2006.01)
 _G01N 30/30_ (2006.01)
 _G01N 30/02_ (2006.01)

(52) U.S. Cl.
 CPC ...... _B01D 53/025_ (2013.01); _G01N 2030/025_ (2013.01); _G01N 2030/3084_ (2013.01)

(58) Field of Classification Search
 CPC ....... G01N 30/6047; G01N 2030/8881; G01N 30/6069
 USPC ...................................................... 73/23.39
 See application file for complete search history.

(56) References Cited

FOREIGN PATENT DOCUMENTS

| | | |
|---|---|---|
| JP | 62-167469 A | 7/1987 |
| JP | 03-004165 A | 1/1991 |

GAS CHROMATOGRAPHY EQUIPMENT

TECHNICAL FIELD

The present invention relates to a gas chromatography equipment including a sample introducer, a separation column, and a detector.

BACKGROUND ART

A gas chromatograph includes a gas introducer for introducing sample gas, a separation column for separating a component from the sample gas, a detector for detecting the separated sample components, and an oven. In a typical conventional gas chromatograph, a separation column is accommodated in a convection oven configured to control the internal temperature by circulating the air heated by a heater with a fan to control the temperature of the separation column.

To this, a gas chromatograph configured to control the temperature of the separation column using an additional mechanism having smaller heat capacity than the convection oven, for example, using a heater wire wound around the separation column, to rapidly increase the temperature of the separation column is proposed (see Patent Literature 1). In this case, the separation column with the heater wire wound therearound is accommodated in separate containers and arranged outside the oven as a column module. To prevent vaporized sample from adhering to inner walls of tubes, a tube connecting a sample introducer and the separation column and a tube connecting the separation column and a detector are accommodated in the oven to the control temperature.

If a portion of the tube connecting the sample introducer and the separation column, or the tube connecting the separation column and the detector is exposed outside the oven, the temperature of the tube drops by radiation and causes effect on analysis results. To avoid such effect, ends of tubes and ends of the separation columns are connected in the oven or in proximity to the oven. In the Patent Literature 1, a column module is attached to the door provided on a side face of the oven so that the column module can replaceably be attached to a housing of the oven.

PRIOR ART DOCUMENT

Patent Document

Patent Literature 1: U.S. Pat. No. 6,530,260

SUMMARY OF THE INVENTION

Problems to be Solved by the Invention

If the column module is attached to the side face of the housing of the oven as mentioned above, a large installation area for the gas chromatography equipment is required, which is disadvantageous. Moreover, when attaching the column module to the door of the housing of the oven as disclosed in Patent Literature 1, the tubes connected to the column module need to be longer than actually required in order to prevent the tubes from interfering with the door when opened or closed.

The object of the present invention is to provide a gas chromatograph capable of controlling the temperature of the separation column with quick response without requiring a large installation area for the gas chromatograph.

Solutions to the Problems

A gas chromatography equipment according to the present invention includes a sample introducer, a detector, a column module, and an oven. The column module accommodates a separation column for separating a component from a sample introduced through the sample introducer and is configured to independently control temperature of the separation column. An end of the separation column is communicated with an end face of the column module, the end face being perpendicular to a main flat surface having the largest area. The oven includes a housing which accommodates at least a part of a tube connecting the sample introducer and the column module and at least a part of a tube connecting the column module and the detector, a heater for heating inside the housing, and a fan for providing mixing inside the housing. A sub-space is provided in a projection section projecting downward from a portion of a bottom face of the housing of the oven. The sub-space communicates with a main space that is a space in the housing other than the sub-space. A column module attaching section for attaching the column module is provided outside the housing and below the main space. A fixed side face of the projection section, which faces the column module attaching section, serves as an attachment face for attaching the column module, where the attachment face is provided with a connection-opening through which an end of a tube in the housing and an end of the separation column are connected. The column module is attached to the housing in such a way that the main flat surface of the column module is horizontally positioned with the end face of the column module through which the end of the separation column is drawn out being the attachment face.

The column module accommodates the separation column in each separately provided container and includes a heater for controlling the temperature inside the container. The column module is configured to connect the end of the separation column and an external tube at the face or in proximity to the face of the container.

Effects of the Invention

The gas chromatography equipment according to the present invention is configured in such a way that the sub-space provided in the projection section projecting downward from a portion of a bottom face of the housing of the oven communicates with a main space, where the main space provided separately from the sub-space and the sub-space constitute the inside of the housing, a column module attaching section for attaching the column module is provided outside the housing and below the main space, a fixed side face, which faces the column module attaching section, of the projection section serves as an attachment face for attaching the column module, the attachment face is provided with a connection-opening through which an end of a tube in the housing and an end of the separation column are connected, and the column module is attached to the housing so that the main flat surface of the column module is horizontally positioned with the end face of the column module through which the end of the separation column is drawn out being the attachment face. The column module can, thus, be arranged below the main space. In this manner, the installation area for the gas chromatography equipment can be made small compared to a gas chromatography equipment configured to attach the column module to a side wall of the oven including only the main space and no sub-space. Since the temperature of the separation column is independently controlled for each column module, the response of the temperature of the separation column to increase or decrease can be improved compared to the configuration with the separation column arranged in the oven. Since the column module is attached to the oven in such a way that the main flat surface is horizontally positioned, the occurrence of the temperature gradient in the main flat surface of the column module caused by heat convection can be avoided, thereby keeping the temperature of the separation column constant in the main flat surface direction of the column module. Since the column module is attached to the fixed side face of the housing, that is, to a wall face which cannot be opened or closed, the tube in the oven need not be longer than required.

EMBODIMENTS OF THE INVENTION

Figure 1:
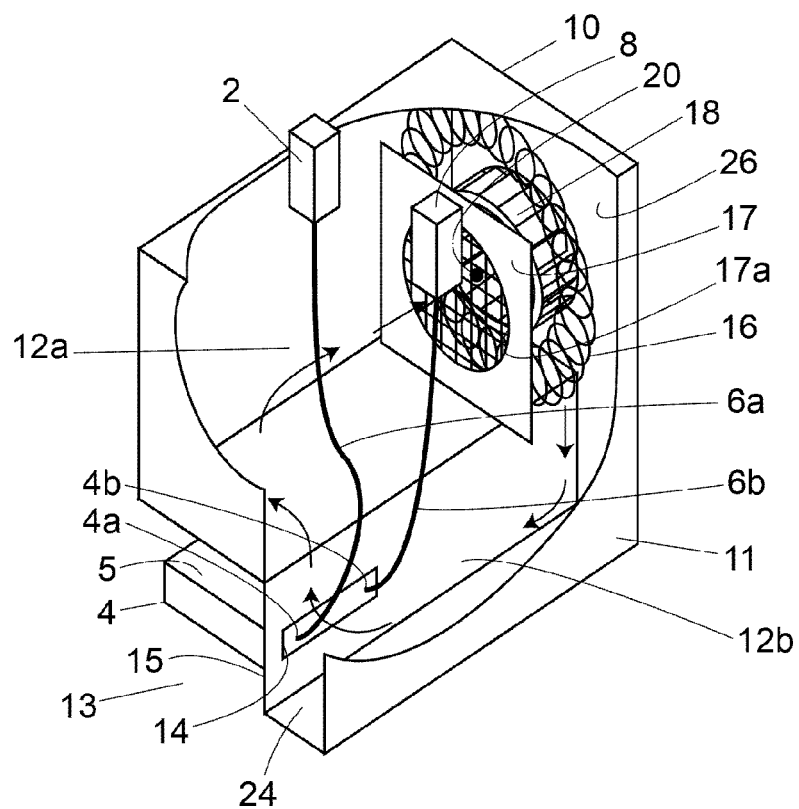
FIG. 1 is a perspective view illustrating a structure of an embodiment of a gas chromatography equipment.

A gas chromatography equipment according to the present invention is preferably configured to accommodate the whole column module below a main space. With this configuration, the column module can be attached within the installation area for the oven, thereby preventing the installation area for the equipment from becoming large.

A plurality of connection-openings is preferably provided in a side face of a projection section of the housing of the oven. With this configuration, a plurality of column modules can be attached to the oven without providing a large installation area for the equipment.

The gas chromatography equipment may be provided that at least a portion of a side face, other than the attachment face of the housing of the oven, perpendicular to the attachment face serves as an open/close side face that can be opened and closed. The open/close side face may constitute a side of the connection-opening so that the column module can be drawn out toward the open/close side face when the open/close side face is opened. In this manner, a tube of the column module can easily be connected and disconnected.

The fan provided in the oven may be, for example, an axial-flow fan. The axial fan may preferably be arranged in a side of the main space of the oven in proximity to a wall face of the housing with a gap between the axial-flow fan and the wall face, and configured to supply air toward the main space and the sub-space along the rotation axis of the axial-flow fan so as to circulate the air heated by the heater. The main space and the sub-space are, thus, heated.

Alternatively, the fan provided in the oven may preferably be, for example, a centrifugal fan. The centrifugal fan may preferably be arranged in a side of the main space of the oven in proximity to the wall face of the housing, and configured to supply air, inhaled from the main space, along the radius of gyration of the centrifugal fan to circulate the air heated by the heater along the wall face. In this manner, the air heated by the heater is sufficiently supplied to the sub-space, thereby uniformly heating the main space and the sub-space to raise the temperature.

More preferably, the embodiment includes a flow control plate arranged in the main space close to the centrifugal fan in such a way that the flow control plate is normal to the rotation axis of the centrifugal fan, where the flow control plate includes an air hole in the location corresponding to the rotation axis of the centrifugal fan and a screening portion surrounding the air hole. The flow control plate restricts the passage of air sent out from the fan to the gap between the screening portion and the wall face of the housing and also restricts the area through which air is inhaled toward the centrifugal fan to the area around the rotation axis of the centrifugal fan. In this manner, the air heated by the heater can surely be supplied to the sub-space, thereby providing uniform temperature inside the oven.

Further, the gas chromatography equipment according to the present invention preferably includes a temperature sensor that is provided in the oven and detects temperature inside the oven and an oven temperature controller that controls the output of the heater or a rotational speed of the fan according to the temperature detected by the temperature sensor. In this manner, the temperature in each of the flow passage connecting the sample introducer and the column module and the flow passage connecting the column module and the detector can be controlled with high accuracy.

An embodiment of the gas chromatography equipment will be described referring to FIG. 1. A portion of the housing of the oven is not illustrated in FIG. 1.

The structure will be described in sequence along the flow of samples. A sample introducer 2 which introduces samples is connected to an injector port 4a of a column module 4 via a capillary (tube) 6a. The ejector port 4b of the column module 4 is connected to a detector 8 via a capillary 6b.

The sample introducer 2 includes, for example, a sample vaporizing chamber for vaporizing a sample by heating. The column module 4 is configured as a flat-box-shaped container with a constant height and accommodates a separation column for separating a component from sample gas. The column module 4 has its own heater (not shown) to independently control the temperature of the separation column. Both ends of the separation column accommodated in the column module 4 are communicated to one of side faces vertical to the main flat surface of the column module 4. The injector port 4a and the ejector port 4b are provided on the side face of the column module 4 so as to realize a connecting to the separation column.

The capillaries 6a and 6b are accommodated in the oven 10. The wall face of the housing of the oven 10 is configured with a metal plate on the surface and a material including insulation in the inner side. The oven 10 includes a projection section 11 projecting downward from the bottom face. The upper part inside the oven 10 forms a main space 12a, and the lower part inside the oven 10, that is, the inside of the projection section 11, forms a sub-space 12b which communicates with the main space 12a.

A heater 16 and a fan 18 are arranged in a side of the main space 12a in the oven 10 and partitioned from the main space 12a by a flow control plate 17. The heater 16 is configured, for example, with a coiled heater wire and arranged so as to surround the outer circumference of the locus of the rotating fan 18. For example, the maximum power consumption (generated heat) of the heater 16 is 500 W. The fan 18 is a centrifugal fan configured to radially generate wind along the radius of gyration of the fan 18 and is arranged in proximity to a wall face 26 of the housing of the oven 10. A temperature sensor 20 is provided in proximity to the heater 16 and the centrifugal fan 18.

The centrifugal fan 18 radially generates wind along the radius of gyration to circulate the air heated by the heater 16 along the wall faces of the housing of the oven 10, from the outside toward the rotation axis of the centrifugal fan 18 as illustrated in arrows in the drawings. The flow control plate 17 provided in the main space 12*a* closer to the centrifugal fan 18 is a sheet member including an air hole 17*a* in the center. The flow control plate 17 is arranged normal to the rotation axis of the centrifugal fan 18. With the flow control plate 17 provided in the main space 12*a* closer to the centrifugal fan 18, the circulating efficiency of the air heated by the heater 16 improves. In this manner, the air heated by the heater 16 uniformly flows in the main space 12*a* and the sub-space 12*b* in the oven 10, thereby suppressing variation in temperature in the oven 10. Through a gap between the outer periphery of the flow control plate 17 and the wall faces of the housing of the oven 10, the air from the centrifugal fan 18 circulates along the wall faces of the housing of the oven 10. The air flowing along the wall faces of the housing of the oven 10 then flows through the air hole 17*a* of the flow control plate 17 to be inhaled in the centrifugal fan 18.

It has been confirmed by measurement that the difference between the temperature in the main space 12*a* and the temperature in the sub-space 12*b* can be controlled within 2° C., when the centrifugal fan 18 is kept rotating at a constant rotational speed of 835 rpm and the target temperature in the oven 10 is set at 200° C. and also at 400° C. Accordingly, even when the projection section 11 is provided in the oven 10, the temperature in the oven 10 can be controlled to be uniform by circulating the air, heated by the heater 16, from outside of the space in the oven 10 with the centrifugal fan 18.

A column module attaching section 13 is located below the main space 12*a* of the oven 10 and beside the projection section 11. A wall face, which constitutes the housing of the oven 10 and faces the column module attaching section 13 of the projection section 11, of the projection section 11 serves as an attachment face 15 for attaching the column module 4. A connection-opening 14 provided in a form of a rectangular penetration hole is provided in the attachment face 15. The column module 4 is attached to the place where the connection-opening 14 is provided on the attachment face 15 in such a way that the main flat surface 5 of the column module 4 is horizontally positioned. The sample introducer 2 and the detector 8 are attached in the upper part of housing of the oven 10.

An end of the capillary 6*a* is connected to the sample introducer 2 at the top surface of the housing of the oven 10, and the other end is connected to the injector port 4*a* of the column module 4 through the connection-opening 14 provided in the side wall of the projection section 11. An end of the capillary 6*b* is connected to the detector 8 at the top surface of the housing of the oven 10, and the other end is connected to the ejector port of the column module 4 through the connection-opening 14.

Figure 2:
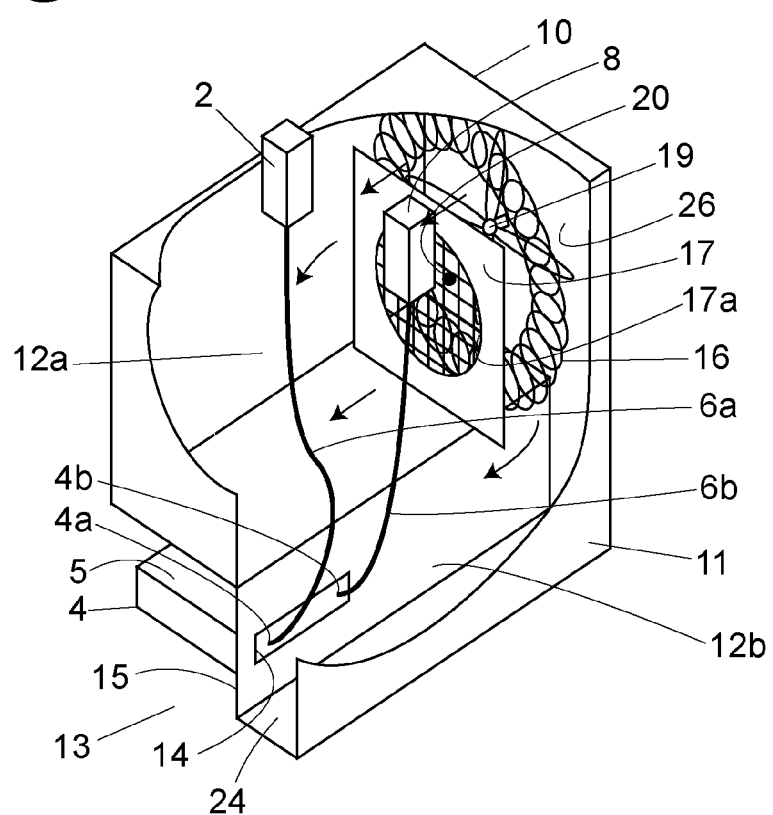
FIG. 2 is a perspective view illustrating a structure of an alternative embodiment of the gas chromatography equipment.

In place of the centrifugal fan 18, an axial-flow fan can be used to circulate the air heated by the heater 16 in the oven 10. In an embodiment illustrated in FIG. 2, an axial-flow fan 19 is used in place of the centrifugal fan 18 in FIG. 1. In the embodiment, the axial-flow fan 19 is provided in the side of the main space 12*a* and partitioned from the main space 12*a* by a flow control plate 17, and configured to generate wind along the axial direction. The air heated by the heater 16 is, thus, supplied to the main space 12*a* and the sub-space 12*b* along the axial direction of the axial-flow fan 19. The performance of the axial-flow fan 19 to supply heated air to the sub-section, however, may be poor compared to that of the centrifugal fan because the axial-flow fan 19 cannot generate wind along the radius of gyration. For this reason, when the volume of the sub-section is large as in an embodiment illustrated in FIG. 4 which will be described later, the centrifugal fan 18 is preferably used.

Figure 3:
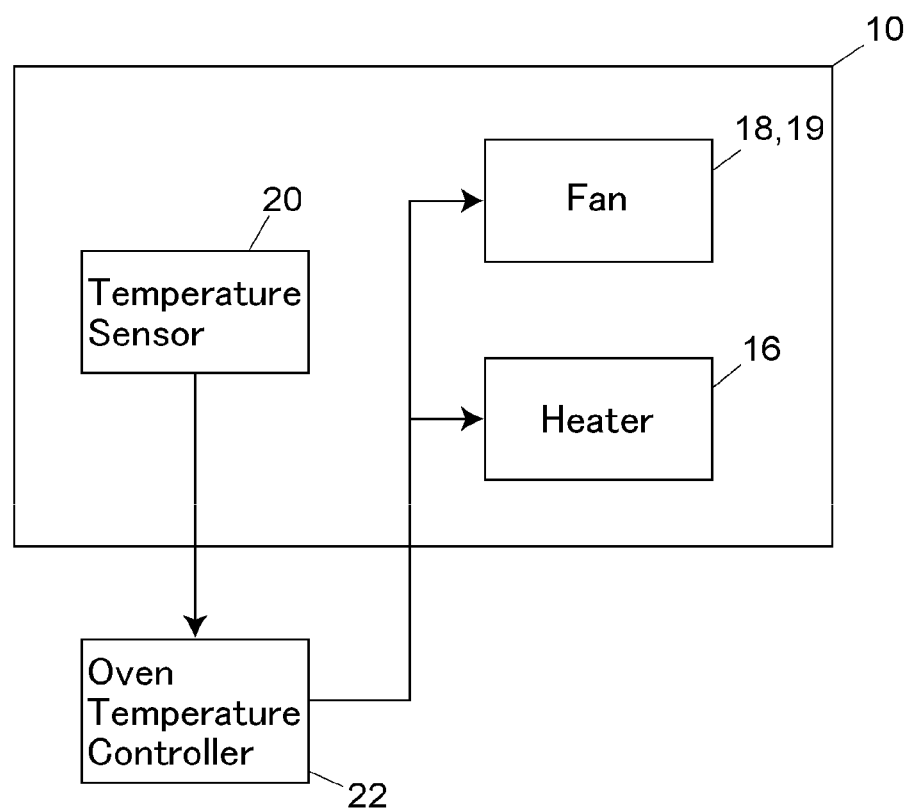
FIG. 3 is a block diagram illustrating a control system of temperature inside an oven of the embodiment.

As illustrated in FIG. 3, the temperature in the oven 10 is adjusted to be constant by the oven temperature controller 22 carrying out feedback control for the output of the heater 16 and the rotational speed of the fan 18 or 19 according to the temperature detected by the temperature sensor 20. The oven temperature controller 22 is configured with a computer dedicated to the gas chromatography equipment or a personal computer connected to the gas chromatography equipment. The oven temperature controller 22 may be configured to control only the output of the heater 16 according to the temperature detected by the temperature sensor 20. In this case, the rotational speed of the fan 18 or 19 is kept constant regardless of the temperature detected by the temperature sensor 20.

Figure 4:
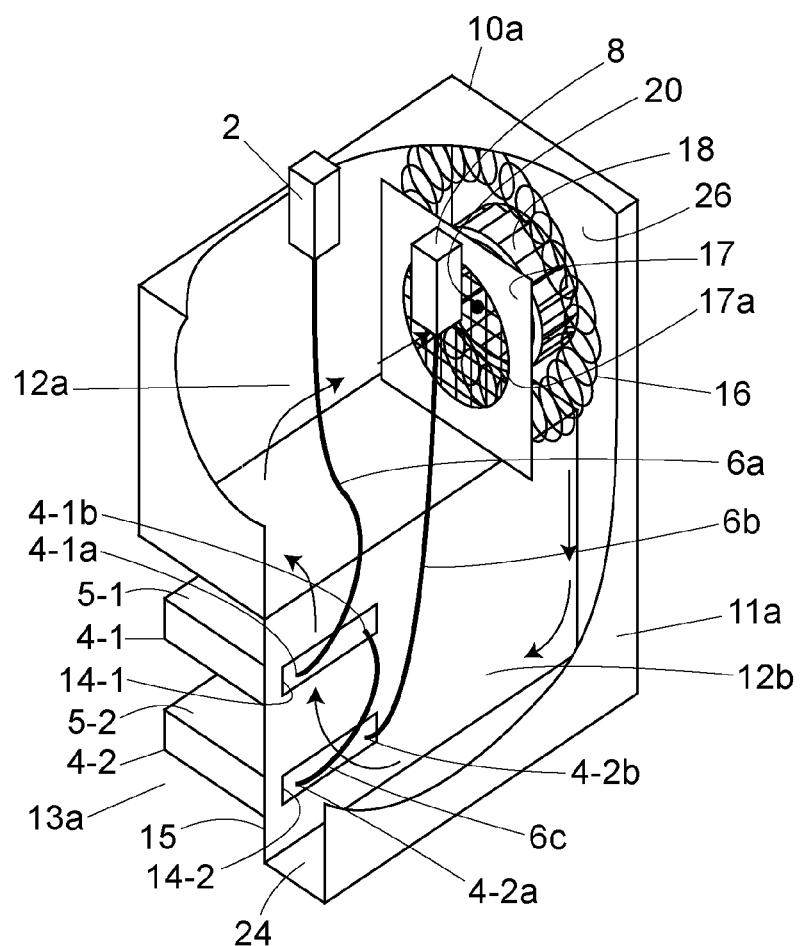
FIG. 4 is a perspective view illustrating a structure of another alternative embodiment of the gas chromatography equipment.

FIG. 4 illustrates a structure of an alternative embodiment of the gas chromatography equipment.

In the embodiment, two column modules 4-1 and 4-2 are provided in a column module attaching section 13*a* of an oven 10*a*. A projection section 11*a* of the oven 10*a* extends downward longer than the embodiments in FIGS. 1 and 2 so that the column modules 4-1 and 4-2 can be vertically arrayed in parallel to be attached to the projection section 11*a*. The wall face, which faces the module attaching section 13*a*, of the projection section 11*a* serves as an attachment face 15 for attaching the column modules 4-1 and 4-2. Vertically arrayed two connection-openings 14-1 and 14-2 are provided in the attachment face 15. The column module 4-1 is attached to the location corresponding to the connection-opening 14-1 and the column module 4-2 is attached to the location corresponding to the connection-opening 14-2 on the wall face of the projection section 11, with main flat surfaces 5-1 and 5-2 of the column modules 4-1 and 4-2 being horizontally positioned.

The capillaries 6*a*, 6*b*, and 6*c* are accommodated in the oven 10*a*. An end of the capillary 6*a* is connected to the sample introducer 2, and the other end is connected to the injector port 4-1*a* of the column module 4-1. An end of the capillary 6*b* is connected to the detector 8, and the other end is connected to the ejector port 4-2*b* of the column module 4-2. An end of the capillary 6*c* is connected to the ejector port 4-1*a* of the column module 4-1, and the other end is connected to the injector port 4-2*a* of the column module 4-2.

In this embodiment, separation columns accommodated in the two column modules 4-1 and 4-2, respectively, are mutually connected in series. The separation column accommodated in the column module 4-1 serves as a first stage separation column, and the separation column accommodated in the column module 4-2 serves as a second stage separation column. Sample gas introduced through the sample introducer 2 travels through the first stage separation column and then through the second stage separation column, and is introduced to the detector 8. The first stage and second stage separation columns have different separating profiles. A component which cannot be separated in the first stage separation column can be separated in the second stage separation column and then introduced to the detector 8.

By providing the projection section 11 or 11a having a wall face configured to attach the column modules 4-1 and 4-2 to the wall face in the lower part of the housing of the oven 10 or 10a as described above, a plurality of column modules can be attached without providing a large installation area for the gas chromatography equipment. With this configuration, without changing the installation area for the equipment, a plurality of stages of separation columns having different separating profiles can be attached to widen a separable range.

When a plurality of vertically arrayed column modules is to be attached, a large vertical dimension is required of the projection section 11a according to the number of column modules to be attached. However, the inside of the oven 10a can uniformly be heated by providing the heater 16 and the centrifugal fan 18 for circulating the air heated by the heater 16 along the wall faces of the housing of the oven 10. The effect can be enhanced by arranging the flow control plate 17 that improves the efficiency of circulating air in the oven 10a.

Figure 5:
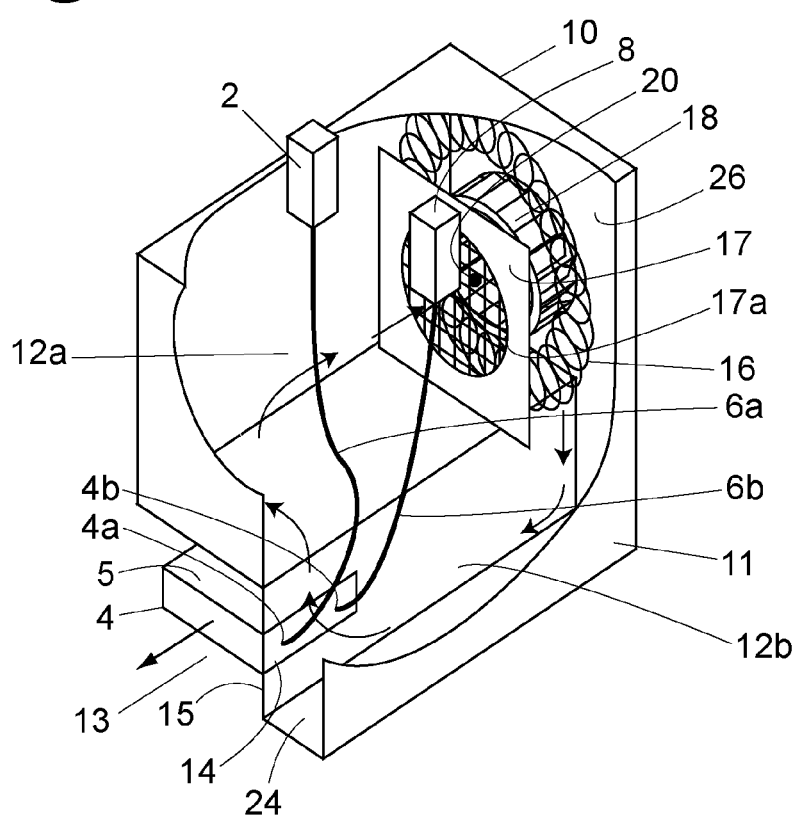
FIG. 5 is a perspective view illustrating a structure of another alternative embodiment of the gas chromatography equipment.

FIG. 5 illustrates an embodiment configured to slide the column module 4 toward the door (open/close side face) 24 of the oven 10 to provide easy attachment and detachment of the column module 4. In the embodiment, at least a portion of the side face in the opposite side to the region provided with the centrifugal fan 18 in the oven 10 serves as an open/close side face 24 allowed to open and close. The open/close side face 24 constitutes a side of the connection-opening 14. When the open/close side face 24 is opened, a side of the connection-opening 14 is removed, allowing the column module 4 to be drawn out toward the open/close side face 24. In this manner, the capillaries 6a and 6b can easily be connected to and disconnected from the column module 4.

This structure can also be applied to an equipment allowing a plurality of column modules to be attached to the oven as illustrated in FIG. 3.

DESCRIPTION OF REFERENCE SIGNS

2 sample introducer
4, 4-1, 4-2 column module
4a, 4-1a, 4-2a injector port (injector port of column module)
4b, 4-1b, 4-2b ejector port (ejector port of column module)
5, 5-1, 5-2 main flat surface (main flat surface of column module)
6a, 6b, 6c capillary (tube)
8 detector
10, 10a oven
11 projection section
12a, main space
12b sub-space
13 column module attaching section
14, 14-1, 14-2 connection-opening
15 attachment face
16 heater
18 centrifugal fan
19 axial-flow fan
20 temperature sensor
22 oven temperature controller
24 open/close side face
24 wall face

The invention claimed is:

1. A gas chromatography equipment comprising:
a sample introducer;
a detector;
a column module accommodating a separation column for separating a component from a sample introduced through the sample introducer, the column module including a heater, being configured to independently control temperature of the separation column by the heater, and an end of the separation column being communicated with an end face, which is perpendicular to a main flat surface having the largest area of the column module; and
an oven including a housing which accommodates at least a portion of a tube connecting the sample introducer and the column module and at least a portion of a tube connecting the column module and the detector, a heater for heating inside the housing, and a fan for providing mixing inside the housing, wherein
a sub-space is provided in a projection section projecting downward from a portion of a bottom face of the housing of the oven, the sub-space communicating with a main space that is a space in the housing other than the sub-space,
a column module attaching section for attaching the column module is provided outside the housing and below the main space,
wherein a fixed side face, which faces the column module attaching section, of the projection section serves as an attachment face for attaching the column module, and wherein the attachment face is provided with a connection-opening through which an end of a tube in the housing and an end of the separation column are connected, and
wherein the column module is attached to the housing in such a way that the main flat surface of the column module is horizontally positioned with the end face of the column module through which the end of the separation column is drawn out being the attachment face.

2. The gas chromatography equipment according to claim 1, wherein a whole of the column module is accommodated below the main space.

3. The gas chromatography equipment according to claim 1, wherein a plurality of connection-openings are provided in the side face of the projection section with respective column module being attached to each connection-opening.

4. The gas chromatography equipment according to claim 1, wherein
at least a portion of a side face, other than the attachment face of the housing of the oven, perpendicular to the attachment face serves as an open/close side face allowed to open and close, and
the open/close side face constitutes a side of the connection-opening so that the column module can be drawn out toward the open/close side face when the open/close side face is opened.

5. The gas chromatography equipment according to claim 1, wherein the fan is an axial-flow fan, arranged in a side of the main space of the oven in proximity to a wall face of the housing with a gap between the fan and the wall face, and configured to circulate air heated by the heater along a rotational axis of the fan.

6. The gas chromatography equipment according to claim 1, wherein the fan is a centrifugal fan arranged in a side of the main space of the oven in proximity to a wall face of the housing, the centrifugal fan being configured to supply air, inhaled from the main space, along a radius of gyration to circulate air heated by the heater along the wall face.

7. The gas chromatography equipment according to claim 6 further comprising,
   a flow control plate arranged in the main space close to the fan so as to be normal to a rotation axis of the fan, the flow control plate including an air hole in a location corresponding to the rotation axis of the fan and the flow control plate restricting an air passage of air sent out from the fan to a gap between the flow control plate and the wall face of the housing and also restricting an area through which air is inhaled toward the fan to an area around the rotation axis of the fan.

8. The gas chromatography equipment according to claim 1, further comprising:
   a temperature sensor that is provided in the oven and detects temperature inside the oven; and
   an oven temperature controller that controls an output of the heater or a rotational speed of the fan according to a temperature detected by the temperature sensor.

* * * * *